US009840556B2

(12) United States Patent
Brown et al.

(10) Patent No.: US 9,840,556 B2
(45) Date of Patent: Dec. 12, 2017

(54) ANTI-TNF ALPHA ANTIBODIES WHICH SELECTIVELY INHIBIT TNF ALPHA SIGNALLING THROUGH THE P55R

(75) Inventors: Derek Thomas Brown, Beenham (GB); Hishani Kirby, Wokingham (GB); Helene Margaret Finney, Berkshire (GB); Alastair David Griffiths Lawson, Hampshire (GB)

(73) Assignee: UCB BIOPHARMA SPRL, Brussels (BE)

( * ) Notice: Subject to any disclaimer, the term of this patent is extended or adjusted under 35 U.S.C. 154(b) by 2195 days.

(21) Appl. No.: 11/791,498

(22) PCT Filed: Nov. 24, 2005

(86) PCT No.: PCT/GB2005/004511
§ 371 (c)(1),
(2), (4) Date: May 24, 2007

(87) PCT Pub. No.: WO2006/056779
PCT Pub. Date: Jun. 1, 2006

(65) Prior Publication Data
US 2008/0124342 A1 May 29, 2008

(30) Foreign Application Priority Data

Nov. 25, 2004 (GB) .................................. 0425972.7

(51) Int. Cl.
*A61K 39/395* (2006.01)
*C07K 16/28* (2006.01)
*C07K 16/24* (2006.01)

(52) U.S. Cl.
CPC ........ *C07K 16/241* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| 5,606,023 | A | 2/1997 | Chen et al. | |
|---|---|---|---|---|
| 7,148,038 | B2 * | 12/2006 | Mather | 435/69.1 |
| 7,250,165 | B2 * | 7/2007 | Heavner et al. | 424/145.1 |
| 7,285,269 | B2 * | 10/2007 | Babcook et al. | 424/142.1 |
| 7,303,885 | B1 * | 12/2007 | Brunner et al. | 435/7.1 |
| 2002/0151682 | A1 | 10/2002 | Athwal et al. | |
| 2004/0110226 | A1 * | 6/2004 | Lazar | C07K 16/00 435/7.1 |

FOREIGN PATENT DOCUMENTS

| EP | 0486908 | 5/1992 |
|---|---|---|
| EP | 0516785 | 12/1992 |
| EP | 0563714 | 10/1993 |
| EP | 0619372 | 10/1994 |
| WO | WO99/59632 | 11/1999 |
| WO | WO03/083061 | 10/2003 |

OTHER PUBLICATIONS

Rudikoff et al. Proc Natl Acad Sci USA 79: 1979-1983, 1982.*
Colman, Research in Immunology 145: 33-36, 1994.*
Kussie et al., J. Immunol. 152: 146-152, 1994.*
Chen, et al., EMBO J., 14: 2784-2794, 1995.*
Rudikoff et al ., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Cope, Andrew P., "Regulation of Autoimmunity by Proinflammatory Cytokines", Current Opinion in Immunology, 1998, vol. 10, pp. 669-676.
Davis, Janice M. et al., "Structure of Human Tumor Necrosis Factor α Derived from Recombinant DNA",. Biochemistry, 1987, vol. 26, pp. 1322-1326.
Banner, David W., "Crystal Structure of the Soluble Human 55 kd TNF Receptor-Human TNFβ Complex: Implications for TNF Receptor Activation", Cell, 1993, vol. 73, pp. 431-445.
Barbara, Jeffrey A.J. et al., "Dissociation of TNF-α Cytotoxic and Proinflammatory Activities by p55 Receptor- and p75 Receptor-Selective TNF-α Mutants", The EMBO Journal, 1994, vol. 13, No. 4, pp. 843-850.
Burress Welborn III, M. et al., "A Human Tumor Necrosis Factor p75 Receptor Agonist Stimulates In Vitro T Cell Proliferation But Does Not Produce Inflammation or Shock in the Baboon", J. Exp. Med., 1996, vol. 184, pp. 165-171.
Jones E. Y. et al., "Structure of Tumour Necrosis Factor", Nature, 1989, vol. 338, pp. 225-228.
Loetscher, Hansruedi et al., "Molecular Cloning and Expression of the Human 55 kd Tumor Necrosis Factor Receptor", Cell., 1990, vol. 61, pp. 351-359.
Mease, Philip J., "Adalimumab: An Anti-TNF Agent for the Treatment of Psoriatic Arthritis", Expert Opin. Biol. Therapy, 2005, vol. 5, No. 11, pp. 1491-1504.
Pennica, Diane et al., "Human Tumour Necrosis Factor: Precursor Structure, Expression and Homology to Lymphotoxin", Nature, 1984, vol. 312, pp. 724-729.
Peschon, Jacques J., "TNF Receptor-Deficient Mice Reveal Divergent Roles for p55 and p75 in Several Models of Inflammation", J. Immunol., 1998, vol. 160, pp. 943-952.
Sheehan, Kathleen C. F. et al., "Monoclonal Antibodies Specific for Murine p55 and p75 Tumor Necrosis Factor Receptors: Identification of a Novel In Vivo Role for p75", J. Exp. Med., 1995, vol. 181, pp. 607-617.
Smith, Craig A. et al., "A Receptor for Tumor Necrosis Factor Defines an Unusual Family of Cellular and Viral Proteins", Science, 1990, vol. 248, pp. 1019-1023.

(Continued)

*Primary Examiner* — Phillip Gambel
(74) *Attorney, Agent, or Firm* — McDonnell Boehnen Hulbert & Berghoff LLP

(57) ABSTRACT

The present invention provides anti-TNFα antibodies which selectively inhibit TNFα signalling through the p55R. In particular the present invention provides anti-TNFα antibodies which selectively inhibit TNFα signalling through the p55R relative to the p75R.

10 Claims, 4 Drawing Sheets

(56) References Cited

OTHER PUBLICATIONS

Figure 1:
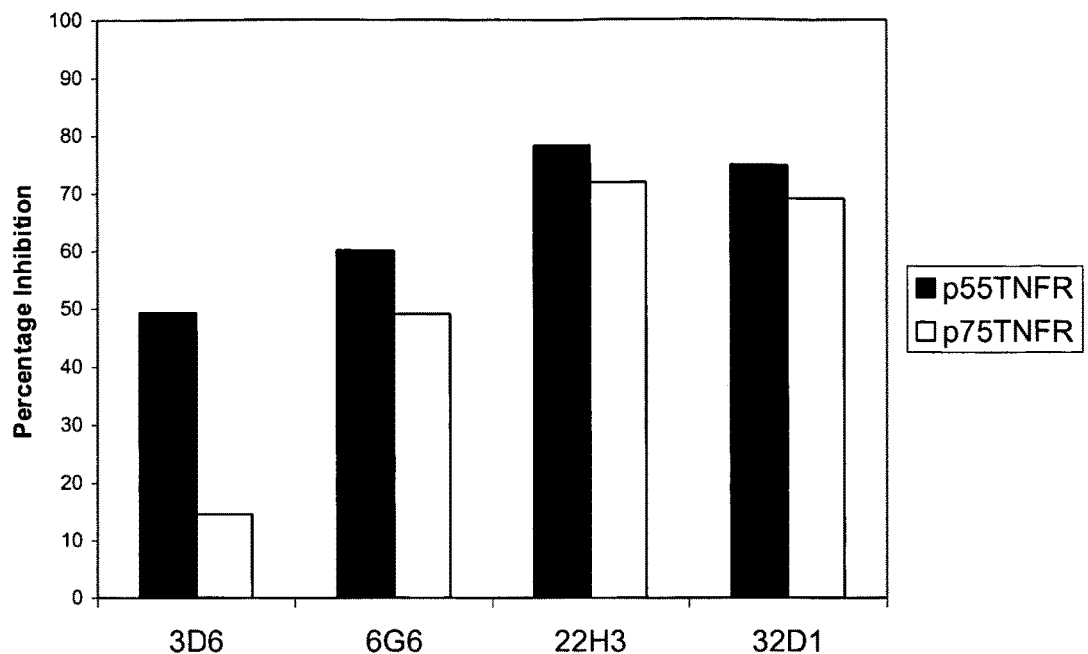

Toussirot, Eric et al., "The Use of TNF-α Blocking Agents in Rheumatoid Arthritis: An Overview", Expert Opin. Pharmacother., 2004, vol. 5, No. 3, pp. 581-594.
Wiendl, Heinz et al., "Therapeutic Approaches in Multiple Sclerosis", Biodrugs, 2002, vol. 16, pp. 183-200.
International Search Report for PCT/GB2005/004511 dated May 22, 2006.
Bloom J.W. et al., "Epitope Mapping and Functional Analysis of Three Murine IgG1 Monoclonal Antibodies to Human Tumor Necrosis Factor-Alpha", Journal of Immunology, vol. 151, No. 5, Sep. 1, 1993, pp. 2707-2716.
Banner et al., "Crystal Structure of the Soluble Human 55kd TNF Receptor-Human TNF-beta Complex: Implications for TNF Receptor Activation" Cell, vol. 73, 431-445, May 7, 1993.
Loetscher, et al., "Human Tumor Necrosis Factor alpha (TNF-alpha) Mutants with Exclusive Specificity for the 55-kDa or 75-kDa TNF Receptors" J. Biol. Chem., vol. 268, No. 35, 26350-26357, Dec. 15, 1993.

\* cited by examiner

SEQUENCE LISTING

<160> NUMBER OF SEQ ID NOS: 23

<210> SEQ ID NO 1
<211> LENGTH: 408
<212> TYPE: DNA
<213> ORGANISM: Rattus rattus

<400> SEQUENCE: 1

```
atggacatca ggctcagctt ggttctcctt gtccttttca taaaaggtgt ccagtgtgag    60
gtgcacctgg tggagtctgg gggaggatta gtgcagcctg aaggtccct gaaactctcc   120 tgcgcagcct caggattcac tttcaataag attccaatgg cctgggtccg ccaggctcca   180
cagaagggtc tggagtgggt cgcatccatt ggttctggtc ctggcgccac ttactatcca   240
gattccgtga agggcagatt tactatctcc agagataatg caagaagcac cctatacctg   300
cagatggaca gtctgagatc tgaggacacg gccacttact tttgtgcaaa acgtacacat   360
actacggact tgattactg gggccaagga gtcatggtca cagtctcg               408
```

<210> SEQ ID NO 2
<211> LENGTH: 136
<212> TYPE: PRT
<213> ORGANISM: Rattus rattus

<400> SEQUENCE: 2

```
Met Asp Ile Arg Leu Ser Leu Val Leu Leu Val Leu Phe Ile Lys Gly
 1               5                  10                  15

Val Gln Cys Glu Val His Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Asn Lys Ile Pro Met Ala Trp Val Arg Gln Ala Pro Gln Lys Gly Leu
    50                  55                  60

Glu Trp Val Ala Ser Ile Gly Ser Gly Pro Gly Ala Thr Tyr Tyr Pro
65                  70                  75                  80

Asp Ser Val Lys Gly Arg Phe Thr Ile Ser Arg Asp Asn Ala Arg Ser
                85                  90                  95

Thr Leu Tyr Leu Gln Met Asp Ser Leu Arg Ser Glu Asp Thr Ala Thr
            100                 105                 110

Tyr Phe Cys Ala Lys Arg Thr His Thr Thr Asp Phe Asp Tyr Trp Gly
        115                 120                 125

Gln Gly Val Met Val Thr Val Ser
    130                 135
```

<210> SEQ ID NO 3
<211> LENGTH: 381
<212> TYPE: DNA
<213> ORGANISM: Rattus rattus

<400> SEQUENCE: 3

```
atgatggctg cacttcaact tttagggctt ttgctgttct gcctcccagc catgagatgt    60
gacatccaga tgacccagtc tcctcactc ctgtcagcat ctgtgggaga cagagtcact   120
ctcagctgca cgcaagtca gaatatttac aacagcttag cctggtatca gcaaaaactt   180
ggaggaactc ccagacccct aatatatagt gcaaatagtt tgcaaacggg catcccgtca   240
aggttcagtg gcagtggatt tggtaccgtt ttcacactca ccatcagcag cctgcagcct   300
gaagatgttg ccacatattt ctgccatcaa tattacagtt ggcccgacac gtttggaact   360
gggaccaagc tggaactgaa a                                             381
```

<210> SEQ ID NO 4
<211> LENGTH: 127
<212> TYPE: PRT
<213> ORGANISM: Rattus rattus

<400> SEQUENCE: 4

```
Met Met Ala Ala Leu Gln Leu Leu Gly Leu Leu Phe Cys Leu Pro
1               5                   10                  15

Ala Met Arg Cys Asp Ile Gln Met Thr Gln Ser Pro Ser Leu Leu Ser
            20                  25                  30

Ala Ser Val Gly Asp Arg Val Thr Leu Ser Cys Asn Ala Ser Gln Asn
            35                  40                  45

Ile Tyr Asn Ser Leu Ala Trp Tyr Gln Gln Lys Leu Gly Gly Thr Pro
50                  55                  60

Arg Pro Leu Ile Tyr Ser Ala Asn Ser Leu Gln Thr Gly Ile Pro Ser
65                  70                  75                  80

Arg Phe Ser Gly Ser Gly Phe Gly Thr Val Phe Thr Leu Thr Ile Ser
                85                  90                  95

Ser Leu Gln Pro Glu Asp Val Ala Thr Tyr Phe Cys His Gln Tyr Tyr
            100                 105                 110

Ser Trp Pro Asp Thr Phe Gly Thr Gly Thr Lys Leu Glu Leu Lys
        115                 120                 125
```

<210> SEQ ID NO 5
<211> LENGTH: 351
<212> TYPE: DNA
<213> ORGANISM: Rattus rattus

<400> SEQUENCE: 5

```
gaggtgcacc tggtggagtc tgggggagga ttagtgcagc ctggaaggtc cctgaaactc      60
tcctgcgcag cctcaggatt cactttcaat aagattccaa tggcctgggt ccgccaggct     120
ccacagaagg gtctggagtg ggtcgcatcc attggttctg gtcctggcgc cacttactat     180
ccagattccg tgaagggcag atttactatc tccagagata atgcaagaag cacccctatac    240
ctgcagatgg acagtctgag atctgaggac acggccactt acttttgtgc aaaacgtaca     300
catactacgg actttgatta ctggggccaa ggagtcatgg tcacagtctc g              351
```

<210> SEQ ID NO 6
<211> LENGTH: 117
<212> TYPE: PRT
<213> ORGANISM: Rattus rattus

<400> SEQUENCE: 6

```
Glu Val His Leu Val Glu Ser Gly Gly Gly Leu Val Gln Pro Gly Arg
1               5                   10                  15

Ser Leu Lys Leu Ser Cys Ala Ala Ser Gly Phe Thr Phe Asn Lys Ile
            20                  25                  30

Pro Met Ala Trp Val Arg Gln Ala Pro Gln Lys Gly Leu Glu Trp Val
            35                  40                  45

Ala Ser Ile Gly Ser Gly Pro Gly Ala Thr Tyr Tyr Pro Asp Ser Val
50                  55                  60

Lys Gly Arg Phe Thr Ile Ser Arg Asp Asn Ala Arg Ser Thr Leu Tyr
65                  70                  75                  80

Leu Gln Met Asp Ser Leu Arg Ser Glu Asp Thr Ala Thr Tyr Phe Cys
                85                  90                  95

Ala Lys Arg Thr His Thr Thr Asp Phe Asp Tyr Trp Gly Gln Gly Val
            100                 105                 110

Met Val Thr Val Ser
        115
```

<210> SEQ ID NO 7

<211> LENGTH: 321
<212> TYPE: DNA
<213> ORGANISM: Rattus rattus

<400> SEQUENCE: 7

```
gacatccaga tgacccagtc tccctcactc ctgtcagcat ctgtgggaga cagagtcact    60
ctcagctgca acgcaagtca gaatatttac aacagcttag cctggtatca gcaaaaactt   120
ggaggaactc ccagacccct aatatatagt gcaaatagtt tgcaaacggg catcccgtca   180
aggttcagtg gcagtggatt tggtaccgtt ttcacactca ccatcagcag cctgcagcct   240
gaagatgttg ccacatattt ctgccatcaa tattacagtt ggcccgacac gtttggaact   300
gggaccaagc tggaactgaa a                                             321
```

<210> SEQ ID NO 8
<211> LENGTH: 107
<212> TYPE: PRT
<213> ORGANISM: Rattus rattus

<400> SEQUENCE: 8

```
Asp Ile Gln Met Thr Gln Ser Pro Ser Leu Leu Ser Ala Ser Val Gly
1               5                   10                  15
Asp Arg Val Thr Leu Ser Cys Asn Ala Ser Gln Asn Ile Tyr Asn Ser
            20                  25                  30
Leu Ala Trp Tyr Gln Gln Lys Leu Gly Gly Thr Pro Arg Pro Leu Ile
        35                  40                  45
Tyr Ser Ala Asn Ser Leu Gln Thr Gly Ile Pro Ser Arg Phe Ser Gly
    50                  55                  60
Ser Gly Phe Gly Thr Val Phe Thr Leu Thr Ile Ser Ser Leu Gln Pro
65                  70                  75                  80
Glu Asp Val Ala Thr Tyr Phe Cys His Gln Tyr Tyr Ser Trp Pro Asp
                85                  90                  95
Thr Phe Gly Thr Gly Thr Lys Leu Glu Leu Lys
            100                 105
```

<210> SEQ ID NO 9
<211> LENGTH: 10
<212> TYPE: PRT
<213> ORGANISM: Rattus rattus

<400> SEQUENCE: 9

```
Gly Phe Thr Phe Asn Lys Ile Pro Met Ala
1               5                   10
```

<210> SEQ ID NO 10
<211> LENGTH: 17
<212> TYPE: PRT
<213> ORGANISM: Rattus rattus

<400> SEQUENCE: 10

```
Ser Ile Gly Ser Gly Pro Gly Ala Thr Tyr Tyr Pro Asp Ser Val Lys
1               5                   10                  15
Gly
```

<210> SEQ ID NO 11
<211> LENGTH: 9
<212> TYPE: PRT
<213> ORGANISM: Rattus rattus

<400> SEQUENCE: 11

Arg Thr His Thr Thr Asp Phe Asp Tyr
1               5

<210> SEQ ID NO 12
<211> LENGTH: 11
<212> TYPE: PRT
<213> ORGANISM: Rattus rattus

<400> SEQUENCE: 12

Asn Ala Ser Gln Asn Ile Tyr Asn Ser Leu Ala
1               5                   10

<210> SEQ ID NO 13
<211> LENGTH: 7
<212> TYPE: PRT
<213> ORGANISM: Rattus rattus

<400> SEQUENCE: 13

Ser Ala Asn Ser Leu Gln Thr
1               5

<210> SEQ ID NO 14
<211> LENGTH: 9
<212> TYPE: PRT
<213> ORGANISM: Rattus rattus

<400> SEQUENCE: 14

His Gln Tyr Tyr Ser Trp Pro Asp Thr
1               5

<210> SEQ ID NO 15
<211> LENGTH: 408
<212> TYPE: DNA
<213> ORGANISM: Rattus rattus

<400> SEQUENCE: 15
atggacttca ggctcagctt ggttctcctt gtccttttca taaaaggtgt ccagtgtgag      60
gtgcacctgg tggagtctgg gggaggatta gtgcagcctg aaggtccct gagactctcc     120
tgcgcagcct caggattcac tttcaataag attccaatgg cctgggtccg ccaggctcca     180
cagaagggtc tggagtgggt cgcatccatt ggttctggtc ctggcaccac ttactatcca     240
gattccgtga agggcagatt tactatctcc agagataatg caagaagcac cctataccctg    300
cagatggaca gtctgagatc tgaggacacg gccacttact tttgtgcaaa acgtacacat     360
actacggact tgattactg gggccaagga gtcatggtca cagtctcg                   408

<210> SEQ ID NO 16
<211> LENGTH: 136
<212> TYPE: PRT
<213> ORGANISM: Rattus rattus

<400> SEQUENCE: 16

Met Asp Phe Arg Leu Ser Leu Val Leu Leu Val Leu Phe Ile Lys Gly
1               5                   10                  15

Val Gln Cys Glu Val His Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asn Lys Ile Pro Met Ala Trp Val Arg Gln Ala Pro Gln Lys Gly Leu
        50                  55                  60

Glu Trp Val Ala Ser Ile Gly Ser Gly Pro Gly Thr Thr Tyr Tyr Pro

```
                65                  70                  75                  80
Asp Ser Val Lys Gly Arg Phe Thr Ile Ser Arg Asp Asn Ala Arg Ser
                    85                  90                  95

Thr Leu Tyr Leu Gln Met Asp Ser Leu Arg Ser Glu Asp Thr Ala Thr
                100                 105                 110

Tyr Phe Cys Ala Lys Arg Thr His Thr Thr Asp Phe Asp Tyr Trp Gly
                115                 120                 125

Gln Gly Val Met Val Thr Val Ser
            130                 135

<210> SEQ ID NO 17
<211> LENGTH: 381
<212> TYPE: DNA
<213> ORGANISM: Rattus rattus

<400> SEQUENCE: 17
atgtatgtgc ccactcaact tttagggctt ttgctgttct gcctcccagc catgagatgt      60
gacatccaga tgacccagtc tccctcactc ctgtcagcat ctgtgggaga cagagtcact     120
ctcagctgca acgcaagtca gaatatttac aacagcttag cctggtatca gcaaaaactt     180
ggaggaactc ccagacccct aatatatagt gcaaatagtt tgcaaacggg catcccgtca     240
aggttcagtg gcagtggatt tggtaccgtt ttcacactca ccatcagcag cctgcagcct     300
gaagatgttg ccacatattt ctgccatcaa tattacagtt ggcccgacac gtttggaact     360
gggaccaaac tggaactgaa a                                               381

<210> SEQ ID NO 18
<211> LENGTH: 127
<212> TYPE: PRT
<213> ORGANISM: Rattus rattus

<400> SEQUENCE: 18

Met Tyr Val Pro Thr Gln Leu Leu Gly Leu Leu Leu Phe Cys Leu Pro
1               5                   10                  15

Ala Met Arg Cys Asp Ile Gln Met Thr Gln Ser Pro Ser Leu Leu Ser
            20                  25                  30

Ala Ser Val Gly Asp Arg Val Thr Leu Ser Cys Asn Ala Ser Gln Asn
        35                  40                  45

Ile Tyr Asn Ser Leu Ala Trp Tyr Gln Gln Lys Leu Gly Gly Thr Pro
    50                  55                  60

Arg Pro Leu Ile Tyr Ser Ala Asn Ser Leu Gln Thr Gly Ile Pro Ser
65                  70                  75                  80

Arg Phe Ser Gly Ser Gly Phe Gly Thr Val Phe Thr Leu Thr Ile Ser
                85                  90                  95

Ser Leu Gln Pro Glu Asp Val Ala Thr Tyr Phe Cys His Gln Tyr Tyr
                100                 105                 110

Ser Trp Pro Asp Thr Phe Gly Thr Gly Thr Lys Leu Glu Leu Lys
            115                 120                 125

<210> SEQ ID NO 19
<211> LENGTH: 351
<212> TYPE: DNA
<213> ORGANISM: Rattus rattus

<400> SEQUENCE: 19
gaggtgcacc tggtggagtc tgggggagga ttagtgcagc ctggaaggtc cctgagactc      60
tcctgcgcag cctcaggatt cactttcaat aagattccaa tggcctgggt ccgccaggct     120
```

```
ccacagaagg gtctggagtg ggtcgcatcc attggttctg gtcctggcac cacttactat    180
ccagattccg tgaagggcag atttactatc tccagagata atgcaagaag caccctatac    240
ctgcagatgg acagtctgag atctgaggac acggccactt actttgtgc aaaacgtaca     300 catactacgg actttgatta ctggggccaa ggagtcatgg tcacagtctc g             351
```

```
<210> SEQ ID NO 20
<211> LENGTH: 117
<212> TYPE: PRT
<213> ORGANISM: Rattus rattus

<400> SEQUENCE: 20
```

Glu Val His Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Lys Ile
            20                  25                  30

Pro Met Ala Trp Val Arg Gln Ala Pro Gln Lys Gly Leu Glu Trp Val
        35                  40                  45

Ala Ser Ile Gly Ser Gly Pro Gly Thr Thr Tyr Tyr Pro Asp Ser Val
    50                  55                  60

Lys Gly Arg Phe Thr Ile Ser Arg Asp Asn Ala Arg Ser Thr Leu Tyr
65                  70                  75                  80

Leu Gln Met Asp Ser Leu Arg Ser Glu Asp Thr Ala Thr Tyr Phe Cys
                85                  90                  95

Ala Lys Arg Thr His Thr Thr Asp Phe Asp Tyr Trp Gly Gln Gly Val
            100                 105                 110

Met Val Thr Val Ser
        115

```
<210> SEQ ID NO 21
<211> LENGTH: 17
<212> TYPE: PRT
<213> ORGANISM: Rattus rattus

<400> SEQUENCE: 21
```

Ser Ile Gly Ser Gly Pro Gly Thr Thr Tyr Tyr Pro Asp Ser Val Lys
1               5                   10                  15

Gly

```
<210> SEQ ID NO 22
<211> LENGTH: 51
<212> TYPE: DNA
<213> ORGANISM: Artificial Sequence
<220> FEATURE:
<223> OTHER INFORMATION: Oligo 4023

<400> SEQUENCE: 22
cgggaagctt ccaccatggc gcccgtcgcc gtctgggccg cgctggccgt c              51

<210> SEQ ID NO 23
<211> LENGTH: 36
<212> TYPE: DNA
<213> ORGANISM: Artificial Sequence
<220> FEATURE:
<223> OTHER INFORMATION: Oligo 4024

<400> SEQUENCE: 23
cccggcgccg tcgccagtgc tcccttcagc tggggg                                36
```

ANTI-TNF ALPHA ANTIBODIES WHICH SELECTIVELY INHIBIT TNF ALPHA SIGNALLING THROUGH THE P55R

This is a National Stage of International Application No. PCT/GB2005/004511, filed Nov. 24, 2005.

The present invention relates to antibodies to TNFα. In particular the present invention relates to antibodies which selectively inhibit TNFα signalling through the p55R relative to the p75R, for example by selectively inhibiting the binding of TNFα to the p55 receptor.

Tumor necrosis factor alpha (TNFα) is a pro-inflammatory cytokine that is released by and interacts with cells of the immune system. TNFα has been shown to be upregulated in a number of human diseases, including chronic diseases such as rheumatoid arthritis, Crohn's disease, ulcerative colitis and multiple sclerosis.

Human TNF-α is a 17 kDa protein and the active form exists as a homotrimer (Pennica et al., 1984, Nature, 312, 724-729; Davis et al., 1987, Biochemistry, 26, 1322-1326; Jones et al., 1989, Nature, 338, 225-228). TNFα exerts its biological effects through interaction with two structurally related but functionally distinct cell surface receptors, p55R and p75R that are co-expressed on most cell types (Loetscher et al., 1990, Cell, 61, 351; Smith et al., 1990, Science, 248, 1019). The p55R is also known as p55TNFR; CD120a; TNFR I; TNFR 1 and TNFRSF1a. The p75R is also known as p75TNFR; CD120b; TNFR II; TNFR 2 and TNFRSF1b. Both receptors are also proteolytically released as soluble molecules capable of binding TNFα. The extracellular domains of the two receptors exhibit sequence similarity, consisting of four repeating cysteine-rich motifs containing four to six cysteines in conserved positions. In contrast their cytoplasmic signalling region sequences are unrelated, suggesting different modes of signalling and function.

The distinct roles of the two receptors were demonstrated by the generation of mice genetically deficient in one or both of the two receptors (Peschon et al., 1998, J. Immunol., 160, 943-952). This study demonstrated that the p55R is responsible for the majority of TNFα-mediated inflammatory responses and the p75R may in some circumstances act to suppress TNFα-mediated inflammatory responses and that the two receptors can act as a balancing system for TNFα action.

Inhibition of TNFα activity as a method of treating disease, in particular, rheumatoid arthritis, has been achieved by a number of different means using inhibitors such as antibodies and soluble receptors. Examples include etanercept, marketed by Immunex Corporation as Enbrel™ which is a recombinant fusion protein comprising two p75 soluble TNF-receptor domains linked to the Fc portion of a human immunoglobulin. Infliximab, marketed by Centocor Corporation as Remicade™ is a chimeric antibody having murine anti-TNFα variable domains and human IgG 1 constant domains. Adalimumab, marketed by Abbott Laboratories as Humira™ is a recombinant, fully human anti-TNFα antibody (Tussirot and Wendling, 2004, Expert Opin. Pharmacother., 5, 581-594). Other inhibitors include engineered TNFα molecules which form trimers with native TNFα and prevent receptor binding (Steed et al., 2003, Science, 301, 1895-1898; WO03033720; WO0164889).

These current methods of inhibiting TNFα activity block binding of TNFα to both the p55 and p75 receptors (see for example Mease, 2005, Expert Opin. Biol. Therapy, 5, 11, 1491-1504). Interestingly, Lenercept and Infliximab have both been shown to exacerbate multiple sclerosis, suggesting that there is also a beneficial role for TNFα in MS (Wiendl and Hohlfeld, 2002, Biodrugs, 16, 183-200). It is now thought that while TNFα signalling through the p55R is necessary for the detrimental effects of TNFα during the acute phase of MS, TNFα signalling through the p75R can lead to beneficial effects such as elimination of inflammatory infiltrates. This immunosuppressive role for TNFα has also been proposed in other autoimmune diseases (Cope, 1998, Current Opinion in Immunology, 10, 669-676). Indeed it has been suggested that p75R agonists could be used to treat allergic conditions such as allergic bronchial asthma (WO99/59632).

The exact mechanism by which the two receptors bind TNFα is not known but one report suggests that both TNFα receptors bind to TNFα using similar interaction sites (Banner et al., 1993, Cell, 73, 431-445). A number of studies using point mutations in the TNFα polypeptide have shown that small areas on surface loops located toward the bottom of the subunit are functionally most relevant. In the trimer, these areas face each other across the surface groove between two subunits. This suggests that one receptor interacts with the sites on two adjacent subunits and that the TNFα trimer has three spatially distinct but equivalent receptor-binding sites. It is not believed to be possible that both receptors can bind the same trimer at the same time (Barbara et al., 1994, EMBO, 13, 843-850).

It has however, been possible to create TNFα mutants which selectively bind to either the p75 or the p55 receptor. TNFα mutants which do not bind to the p55R but do bind to the p75R have been demonstrated to retain antitumor activity but exhibit reduced proinflammatory activities (Barbara et al., 1994, EMBO J, 13, 843-850). This has led to these p75R selective TNFα mutants being investigated for use in anti-cancer therapies in order to avoid the systemic toxicity that is seen with native TNFα (Burress Welborn III, et al., 1996, J. Exp. Med., 184, 165-171; U.S. Pat. No. 5,606,023; EP0486908; EP0619372; EP0563714).

It would be desirable, for the treatment of certain autoimmune diseases, such as MS, and certain inflammatory diseases, to be able to selectively inhibit TNFα signalling through the p55R whilst leaving TNFα signalling through the p75R largely unaffected.

Selective inhibition of signalling through the p55R could be achieved using a p55 receptor specific antibody. To date only antibodies selective for the murine p55 and p75 receptors have been isolated (Sheehan et al., 1995, J. Exp. Med. 181, 607-617). There are however potential disadvantages associated with using anti-receptor antibodies as these may also bind to soluble forms of the receptors, reducing the effectiveness of the antibodies as well as losing the protective effects of the soluble receptors. In addition there is also the risk that the antibodies could in themselves cause signalling once bound to the receptor i.e. be agonistic. Also, since the p55R is found on most cell types in the body albeit at low levels, large doses of antibody may be required to achieve sufficient blocking of p55R signalling. It may therefore be better to selectively block the signalling of the less abundant ligand, TNFα through the p55R instead, for example by blocking binding to the p55R. To date there have been no reports of anti-TNFα antibodies which selectively inhibit TNFα signalling through the p55R whilst retaining TNFα signalling through the p75R.

Surprisingly, despite the p55 and p75 receptors apparently sharing the same binding site on the TNFα trimer, we have been able to demonstrate that it is possible to isolate an anti-TNFα antibody which selectively inhibits TNFα signalling through the p55R for example by selectively inhibiting the binding of TNFα to the p55R. Hence the present invention provides an anti-TNFα antibody that selectively inhibits TNFα signalling through the p55R. In particular, the anti-TNFα antibody of the present invention selectively inhibits TNFα signalling through the p55R relative to the p75R. The antibodies of the present invention therefore have the advantageous property that they can selectively inhibit the effects of TNFα mediated by the p55R whilst retaining the beneficial effects of TNFα signalling through the p75R. Accordingly, the present invention also provides the use of an anti-TNFα antibody that selectively inhibits TNFα signalling through the p55R for the manufacture of a medicament for the treatment and/or prophylaxis of an autoimmune or inflammatory disease. Also provided is a method for the treatment and/or prophylaxis of an autoimmune or inflammatory disease in a subject comprising administering to said subject a therapeutically effective amount of an antibody that selectively inhibits TNFα signalling through the p55R.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

The anti-TNFα antibodies of the present invention selectively bind to TNFα. Selectively binding means that the antibodies have a greater affinity for TNFα polypeptides than for other polypeptides. Preferably the TNFα polypeptide is human TNFα.

TNFα polypeptide or cells expressing said polypeptide can be used to produce anti-TNFα antibodies which specifically recognise said polypeptide. The TNFα polypeptide may be a 'mature' polypeptide or a biologically active fragment or derivatives thereof which include the receptor binding site. Preferably the TNFα polypeptide is the mature polypeptide. TNFα polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The TNFα polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Anti-TNFα antibodies for use in the present invention include whole antibodies and functionally active fragments or derivatives thereof and may be, but are not limited to, monoclonal, multi-valent, multi-specific, humanized or chimeric antibodies, single chain antibodies, Fab fragments, Fab' and F(ab')$_2$ fragments, fragments produced by a Fab expression library, anti-idiotypic (anti-Id) antibodies, and epitope-binding fragments of any of the above. Particular antibody fragments also include those described in International patent applications WO2005003169, WO2005003170 and WO2005003171 (all published on 13 Jan. 2005). Antibody fragments and methods of producing them are well known in the art, see for example Verma et al., 1998, Journal of Immunological Methods, 216, 165-181.

Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. Variants of these constant region domains may also be used. For example IgG molecules in which the serine at position 241 has been changed to proline as described in Angal et al., Molecular Immunology, 1993, 30 (1), 105-108. Particularly preferred is the IgG4 constant domain comprising this change.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to the TNFα polypeptide. Also, transgenic mice, or other organisms, including other mammals, may be used to express humanized antibodies.

In one embodiment the present invention provides an anti-TNFα antibody which selectively inhibits TNFα signalling through the p55R, comprising a heavy chain, wherein the variable domain of the heavy chain comprises at least one of a CDR having the sequence given in SEQ ID NO:9 for CDR-H1, a CDR having the sequence given in SEQ ID NO:10 or SEQ ID NO:21 for CDR-H2 and a CDR having the sequence given in SEQ ID NO:11 for CDR-H3.

In one example an antibody of the present invention comprises a heavy chain wherein at least two of CDR-H1, CDR-H2 and CDR-H3 of the variable domain of the heavy chain are selected from the following: the sequence given in SEQ ID NO:9 for CDR-H1, the sequence given in SEQ ID NO:10 or SEQ ID NO:21 for CDR-H2 and the sequence given in SEQ ID NO:11 for CDR-H3. For example, the antibody may comprise a heavy chain wherein CDR-H1 has the sequence given in SEQ ID NO:9 and CDR-H2 has the sequence given in SEQ ID NO:10. Alternatively, the antibody may comprise a heavy chain wherein CDR-H1 has the sequence given in SEQ ID NO:9 and CDR-H3 has the sequence given in SEQ ID NO11, or the antibody may comprise a heavy chain wherein CDR-H2 has the sequence given in SEQ ID NO:21 and CDR-H3 has the sequence given in SEQ ID NO:11. For the avoidance of doubt, it is understood that all permutations are included.

In one embodiment an antibody according to the present invention comprises a heavy chain, wherein the variable domain comprises the sequence given in SEQ ID NO:9 for CDR-H1, the sequence given in SEQ ID NO:10 for CDR-H2 and the sequence given in SEQ ID NO:11 for CDR-H3.

In one embodiment an antibody according to the present invention comprises a heavy chain, wherein the variable domain comprises the sequence given in SEQ ID NO:9 for CDR-H1, the sequence given in SEQ ID NO:21 for CDR-H2 and the sequence given in SEQ ID NO:11 for CDR-H3.

In one embodiment, the antibody of the present invention comprises a heavy chain, wherein the variable domain of the heavy chain comprises the sequence given in SEQ ID NO:6.

In one embodiment, the antibody of the present invention comprises a heavy chain, wherein the variable domain of the heavy chain comprises the sequence given in SEQ ID NO:20.

In another embodiment, the antibody of the present invention comprises a heavy chain, wherein the variable domain of the heavy chain comprises a sequence having at least 60% identity or similarity to the sequence given in SEQ ID NO:6 or the sequence given in SEQ ID NO:20. In one embodiment, the antibody of the present invention comprises a heavy chain, wherein the variable domain of the heavy chain comprises a sequence having at least 90%, 95% or 98% identity or similarity to the sequence given in SEQ ID NO:6 or the sequence given in SEQ ID NO:20.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The present invention also provides an anti-TNFα antibody which selectively inhibits TNFα signalling through the p55R, comprising a light chain, wherein the variable domain of the light chain comprises at least one of a CDR having the sequence given in SEQ ID NO:12 for CDR-L1, a CDR having the sequence given in SEQ ID NO:13 for CDR-L2 and a CDR having the sequence given in SEQ ID NO:14 for CDR-L3.

In one embodiment the antibody of the present invention comprises a light chain, wherein at least two of CDR-L1, CDR-L2 and CDR-L3 of the variable domain of the light chain are selected from the following: the sequence given in SEQ ID NO:12 for CDR-L1, the sequence given in SEQ ID NO:13 for CDR-L2 and the sequence given in SEQ ID NO:14 for CDR-L3. For example, the antibody may comprise a light chain wherein CDR-L1 has the sequence given in SEQ ID NO:12 and CDR-L2 has the sequence given in SEQ ID NO:13. Alternatively, the antibody may comprise a light chain wherein CDR-L1 has the sequence given in SEQ ID NO:12 and CDR-L3 has the sequence given in SEQ ID NO:14, or the antibody may comprise a light chain wherein CDR-L2 has the sequence given in SEQ ID NO:13 and CDR-L3 has the sequence given in SEQ ID NO:14. For the avoidance of doubt, it is understood that all permutations are included.

In one example the antibody of the present invention comprises a light chain, wherein the variable domain comprises the sequence given in SEQ ID NO:12 for CDR-L1, the sequence given in SEQ ID NO:13 for CDR-L2 and the sequence given in SEQ ID NO:14 for CDR-L3.

In one embodiment, the present invention comprises a light chain, wherein the variable domain of the light chain comprises the sequence given in SEQ ID NO:8.

In another embodiment, the antibody of the present invention comprises a light chain, wherein the variable domain of the light chain comprises a sequence having at least 60% identity or similarity to the sequence given in SEQ ID NO:8. Preferably, the antibody of comprises a light chain, wherein the variable domain of the light chain comprises a sequence having at least 90%, 95% or 98% identity or similarity to the sequence given in SEQ ID NO:8.

The antibody molecules of the present invention preferably comprise a complementary light chain or a complementary heavy chain, respectively.

In one embodiment the antibody of the present invention comprises a heavy chain, wherein the variable domain of the heavy chain comprises the sequence given in SEQ ID NO:9 for CDR-H1, the sequence given in SEQ ID NO:10 or SEQ ID NO:21 for CDR-H2 and the sequence given in SEQ ID NO:11 for CDR-H3 and a light chain wherein the variable domain of the light chain comprises the sequence given in SEQ ID NO:12 for CDR-L1, the sequence given in SEQ ID NO:13 for CDR-L2 and the sequence given in SEQ ID NO:14 for CDR-L3.

In one embodiment the antibody comprises a heavy chain, wherein the variable domain of the heavy chain comprises the sequence given in SEQ ID NO:6 and a light chain, wherein the variable domain of the light chain comprises the sequence given in SEQ ID NO:8.

In one embodiment the antibody comprises a heavy chain, wherein the variable domain of the heavy chain comprises the sequence given in SEQ ID NO:20 and a light chain, wherein the variable domain of the light chain comprises the sequence given in SEQ ID NO:8.

In one further embodiment of the invention, the antibody comprises a heavy chain and a light chain, wherein the variable domain of the heavy chain comprises a sequence having at least 60% identity or similarity to the sequence given in SEQ ID NO:6 and the variable domain of the light chain comprises a sequence having at least 60% identity or similarity to the sequence given in SEQ ID NO:8. Preferably, the antibody comprises a heavy chain, wherein the variable domain of the light chain comprises a sequence having at least 90%, 95% or 98% identity or similarity to the sequence given in SEQ ID NO:6 and a light chain, wherein the variable domain of the light chain comprises a sequence having at least 90%, 95% or 98% identity or similarity to the sequence given in SEQ ID NO:8.

In one further embodiment of the invention, the antibody comprises a heavy chain and a light chain, wherein the variable domain of the heavy chain comprises a sequence having at least 60% identity or similarity to the sequence given in SEQ ID NO:20 and the variable domain of the light chain comprises a sequence having at least 60% identity or similarity to the sequence given in SEQ ID NO:8. Preferably, the antibody comprises a heavy chain, wherein the variable domain of the light chain comprises a sequence having at least 90%, 95% or 98% identity or similarity to the sequence given in SEQ ID NO:20 and a light chain, wherein the variable domain of the light chain comprises a sequence having at least 90%, 95% or 98% identity or similarity to the sequence given in SEQ ID NO:8.

One antibody provided by the present invention is referred to herein as antibody '462'. The complete nucleotide and amino acid sequences of the heavy chain variable domain of rat antibody '462' are given in SEQ ID NOS: 5 and 6 and the complete nucleotide and amino acid sequences of the light chain variable domain of rat antibody '462' are given in SEQ ID NOS: 7 and 8. The nucleotide and amino acid sequences of the heavy chain variable region of this antibody including the rat leader sequence are given in SEQ ID NOs: 1 and 2 and the light chain variable regions are given in SEQ ID NOs:3 and 4.

Another antibody provided by the present invention is referred to herein as antibody '463'. The complete nucleotide and amino acid sequences of the heavy chain variable domain of rat antibody '463' are given in SEQ ID NOS: 19 and 20 and the complete nucleotide and amino acid sequences of the light chain variable domain of rat antibody '463' are given in SEQ ID NOS: 7 and 8. The nucleotide and amino acid sequences of the heavy chain variable region of this antibody including the rat leader sequence are given in SEQ ID NOs: 15 and 16 and the light chain variable regions are given in SEQ ID NOs:17 and 18.

Also provided by the present invention is a CDR-grafted (or humanised) anti-TNFα antibody characterised in that the antibody selectively inhibits TNFα signalling through the p55R. In one embodiment one or more of the CDRs in the CDR-grafted antibody molecule have been obtained from either of the rat antibodies 462 or 463. The CDRs of rat antibody 462 are provided in SEQ ID NOS:9, 10, 11, 12, 13 and 14. The CDRs of rat antibody 463 are provided in SEQ ID NOS:9, 21, 11, 12, 13 and 14. As used herein, the term 'CDR-grafted antibody molecule' refers to an antibody molecule wherein the heavy and/or light chain contains one or more CDRs (including, if desired, one or more modified CDRs) from a donor antibody (e.g. a rat antibody such as antibody '462' or '463' as described herein) grafted into a heavy and/or light chain variable region framework of an acceptor antibody (e.g. a human antibody). For a review, see Vaughan et al, Nature Biotechnology, 16, 535-539, 1998.

When the CDRs are grafted, any appropriate acceptor variable region framework sequence may be used having regard to the class/type of the donor antibody from which the CDRs are derived, including mouse, primate and human framework regions. Preferably, the CDR-grafted antibody of the present invention has a variable domain comprising human acceptor framework regions as well as one or more of the CDRs derived from the donor antibody as referred to above. Thus, provided is a CDR-grafted antibody wherein the variable domain comprises human acceptor framework regions and non-human, preferably rat, donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Donor residues are residues from the donor antibody, i.e. the antibody from which the CDRs were originally derived, which may in one embodiment of the present invention be either of the rat antibodies '462' or '463' as described herein.

The antibody molecule of any aspect of the present invention preferably has a high binding affinity for TNFα, preferably picomolar. Preferably the antibody molecule of the present invention has a binding affinity of between about 1 and 500 μM. In one embodiment the antibody molecule of the present invention has a binding affinity of between about 10 and about 400 pM. It will be appreciated that the affinity of antibodies provided by the present invention may be altered using any suitable method known in the art. The present invention therefore also relates to variants of the antibody molecules of the present invention, which have an improved affinity for TNFα. Where necessary the affinity of the antibody for use in the present invention may be improved by using affinity maturation protocols known in the art, such as mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The anti-TNFα antibodies provided by the present invention selectively inhibit TNFα signalling through the p55R, for example by selectively inhibiting the binding of TNFα to the p55R i.e. they reduce the signalling through this receptor. The term 'selectively inhibit' means that the antibodies of the present invention inhibit TNFα signalling through the p55R to a greater extent than they inhibit TNFα signalling through the p75R. Hence in one embodiment, the invention provides an anti-TNFα antibody which selectively inhibits TNFα signalling through the p55R relative to the p75R. Preferably the antibody substantially reduces TNFα signalling through the p55R. In one example the antibody of the present invention substantially reduces binding of TNFα to the p55R. In one example the antibodies of the present invention inhibit binding of TNFα to the p55R by more than they inhibit binding of TNFα to the p75R. It will be understood that the term 'inhibit' as used herein includes total and partial inhibition. Hence the term includes total and partial inhibition of TNFα signalling through the p55R. It will be appreciated that the extent of inhibition may be affected by the concentration of antibody used.

In one embodiment the anti-TNFα antibody inhibits TNFα signalling through the p55R by greater than 40%, preferably between 40 and 100%, even more preferably between 45 and 100%. In one embodiment the anti-TNFα antibody inhibits TNFα signalling through the p55R by 50% or greater. In one embodiment the anti-TNFα antibody inhibits TNFα signalling through the p55R by 60% or greater. In one embodiment the anti-TNFα antibody inhibits TNFα signalling through the p55R by 70% or greater. In one embodiment the anti-TNFα antibody inhibits TNFα signalling through the p55R by 80% or greater. In one embodiment the anti-TNFα antibody inhibits TNFα signalling through the p55R by 90% or greater.

In one example the anti-TNFα antibody of the present invention reduces the binding of TNFα to the p55R by greater than 40%, preferably between 40 and 100%, even more preferably between 45 and 100%.

Preferably the anti-TNFα antibody of the present invention leaves TNFα signalling through the p75R largely unaffected. Preferably the anti-TNFα antibody of the present invention reduces TNFα signalling through the p75R by no more than around 50%, preferably by between 0 and 50%. In one example the anti-TNFα antibody of the present invention reduces TNFα signalling through the p75R by no more than around 40%. In one example the anti-TNFα antibody of the present invention reduces TNFα signalling through the p75R by no more than around 30%. In one example the anti-TNFα antibody of the present invention reduces TNFα signalling through the p75R by no more than around 20%. In one example the anti-TNFα antibody of the present invention reduces TNFα signalling through the p75R by no more than around 10%.

In one example the anti-TNFα antibody of the present invention leaves the binding of TNFα to the p75R largely unaffected. Preferably the anti-TNFα antibody of the present invention reduces binding of TNFα to the p75R by no more than around 30%, preferably by between 0 and 30%, more preferably by between 0 and 20%, even more preferably by between 0 and 15%.

Accordingly, in one example, at the concentration at which an anti-TNFα antibody of the present invention inhibits TNFα signalling through the p55R by 50%, TNFα signalling through the p75R is reduced by no more than 40%, generally by no more than 30%, usually by no more than 25%, typically by no more than 20%, ideally by no more than 10%.

In one example, the concentration of antibody required to inhibit TNFα signalling by 50% is quoted as the $IC_{50}$. Accordingly, in one example the anti-TNFα antibody of the present invention has an $IC_{50}$ for TNFα signalling through the p55R which is at least 5 fold lower, generally at least 10 fold lower, typically at least 15 fold lower, usually at least 20 fold lower, ideally at least 50 fold lower, preferably at least 100 fold lower than its $IC_{50}$ for TNFα signalling through the p75R. The skilled person will appreciate that a lower $IC_{50}$ figure denotes a more active compound.

To identify anti-TNFα antibodies which selectively inhibit TNFα signalling through the p55R, for example by inhibiting binding of TNFα to the p55R a number of different approaches may be taken by those skilled in the art. In one example antibodies with these properties are identified by first identifying antibodies that interact with TNFα and subsequently testing those antibodies to identify those that selectively inhibit TNFα signalling through the p55R. In another example antibodies are identified by first identifying antibodies that interact with TNFα and subsequently testing those antibodies to identify those that selectively inhibit the binding of TNFα to the p55R and optionally further screening those antibodies for selective inhibition of signalling. Alternatively, antibodies may be screened directly to identify those that selectively inhibit TNFα signalling through the p55R relative to the p75R, for example by screening directly in signalling and/or binding assays.

Antibodies that interact with TNFα may be identified using any suitable method, for example by using an assay system where the TNFα polypeptide is contacted with a candidate antibody and the ability of the candidate antibody to interact with the TNFα polypeptide is determined. Preferably, the ability of a candidate antibody to interact with a TNFα polypeptide is compared to a reference range or control. If desired, this assay may be used to screen a plurality of candidate antibodies using a plurality of TNFα polypeptide samples. In one example, a first and second sample comprising native or recombinant TNFα polypeptide are contacted with a candidate antibody or a control agent and the ability of the candidate antibody to interact with the TNFα polypeptide is determined by comparing the difference in interaction between the candidate antibody and the control agent. Preferably, the TNFα polypeptide is first immobilized, by, for example, contacting the polypeptide with an immobilized antibody which specifically recognizes and binds it, or by contacting a purified preparation of TNFα polypeptide with a surface designed to bind proteins. The TNFα polypeptide may be partially or completely purified (e.g. partially or completely free of other polypeptides) or part of a cell lysate. Further, the polypeptide may be a fusion protein comprising the TNFα polypeptide or a biologically active portion thereof and a domain such as glutathionine-S-transferase or the Fc region of IgG1. Alternatively, the polypeptide can be biotinylated using techniques well known to those of skill in the art (e.g. biotinylation kit, Pierce Chemicals; Rockford, Ill.). In some instances, the TNFα polypeptide or the candidate antibody is labelled, for example with a radioactive label (such as $^{32}P$, $^{35}S$ or $^{125}I$), or a fluorescent label (such as fluorescein isothiocyanate, rhodamine, phycoerythrin, phycocyanin, allophycocyanin, o-phthaldehyde or fluorescamine) to enable detection of an interaction between the TNFα polypeptide and a candidate antibody. The ability of the candidate antibody to interact with the TNFα polypeptide can be determined by methods known to those of skill in the art, for example, ELISA, BIAcore™, Flow cytometry or fluorescent microvolume assay technology (FMAT).

As described above, antibodies may be pre-screened to identify antibodies that bind TNFα prior to screening those antibodies which bind for their ability to selectively inhibit TNFα signalling through the p55R.

In one embodiment the antibodies of the present invention selectively inhibit TNFα signalling through the p55R by inhibiting binding of TNFα to the p55R. Antibodies which selectively inhibit the binding of TNFα to the p55R may be identified by any suitable method, for example by:
  (i) comparing the binding of TNFα to the p55R in the presence of a candidate antibody with the binding of TNFα to the p55R in the absence of the candidate antibody or in the presence of a control agent; and
  (ii) comparing the binding of TNFα to the p75R in the presence of the candidate antibody with the binding of TNFα to the p75R in the absence of the candidate antibody or in the presence of a control agent; and
  (iii) determining whether the candidate antibody substantially inhibits the binding of TNFα to the p55R relative to the p75R.

Such assays can be used to screen candidate agents, in clinical monitoring and/or in drug development.

Examples of suitable TNFα receptor (p55R and p75R) binding inhibition assays have been described, see for example U.S. Pat. No. 5,606,023 and Loetscher et al., 1993, The Journal of Biological Chemistry, 268, 26350-26357. Further examples of suitable cell-free and cell-based assays are provided in the Examples.

Preferably, the ability of a candidate antibody to selectively inhibit the binding of TNFα to the p55R is compared to a reference range or control. If desired, this assay may be used to screen a plurality of candidate antibodies using a plurality of receptor binding inhibition assays. In one example of a cell free assay, a first and second sample comprising native or recombinant TNFα polypeptide are contacted with a candidate antibody or a control agent and the ability of the candidate antibody to inhibit the binding of the TNFα polypeptide to either the p55R or p75R is determined by comparing the difference in binding of TNFα to each receptor in the presence of the candidate antibody and a control agent. In one example of such an assay the extracellular domain of the receptor polypeptide is first immobilized, by, for example, contacting the extracellular domain of the appropriate receptor with an immobilized antibody which specifically recognizes and binds it, or by contacting a purified preparation of the receptor polypeptide with a surface designed to bind proteins. The receptor polypeptide may be partially or completely purified (e.g. partially or completely free of other polypeptides) or part of a cell lysate. Further, the receptor polypeptide may be a fusion protein comprising the extracellular domain of the receptor or a biologically active portion thereof and a domain such as glutathionine-S-transferase or the Fc portion of IgG1. Alternatively, the receptor polypeptide can be biotinylated using techniques well known to those of skill in the art (e.g. biotinylation kit, Pierce Chemicals; Rockford, Ill.). The ability of the candidate antibody to inhibit the binding of TNFα to the immobilised p55 or p75 receptors can be determined by methods known to those of skill in the art, for example, ELISA, BIAcore™, Flow cytometry or fluorescent microvolume assay technology (FMAT).

In another example of a cell free assay the TNFα polypeptide is first immobilized, by, for example, contacting the polypeptide with an immobilized antibody which specifically recognizes and binds it, or by contacting a purified preparation of TNFα polypeptide with a surface designed to bind proteins. The ability of a candidate antibody to selectively inhibit the binding of TNFα to the p55R or p75R can be determined by incubating the candidate antibody with the immobilised TNFα polypeptide, contacting the TNFα polypeptide with either the p55R or the p75R polypeptide and detecting whether the receptor has bound to the TNFα polypeptide. The p55R and p75R polypeptides may each be a fusion protein comprising the extracellular domain of the receptor or a biologically active portion thereof and a domain such as the Fc portion of IgG1. Receptor binding may be detected by using for example anti-IgG Fc antibodies which bind to the Fc portion of the receptor fusion protein conjugated to a reporter group such as peroxidase. The presence or absence of receptor binding can be used to determine whether the candidate antibody has selectively blocked the binding of TNFα to the p55R.

In another example, where a cell-based assay is used, a population of cells expressing either the p55R or p75R is contacted with TNFα and a candidate antibody and the ability of the candidate antibody to inhibit the binding of TNFα to the receptor is determined. Preferably, the ability of a candidate antibody to inhibit TNFα binding is compared to a reference range or control. The cell, for example, can be of eukaryotic origin (e.g. yeast or mammalian) and can express the p55R or p75R endogenously or be genetically engineered to express the polypeptide. In some instances, the TNFα polypeptide is labelled, for example with a radioactive label (such as $^{32}P$, $^{35}S$ or $^{125}I$ or a fluorescent label (such as fluorescein isothiocyanate, rhodamine, phycoerythrin, phycocyanin, allophycocyanin, o-phthaldehyde or fluorescamine) to enable detection of an interaction between the TNFα polypeptide and the receptor. Alternative methods such as ELISA, flow cytometry and FMAT may also be used.

Antibodies which selectively inhibit TNFα signalling through the p55R, for example by selectively inhibiting binding of TNFα to the p55R may be identified using cell based signalling assays.

In one example, L929 cells (a mouse fibroblast cell line) which express the mouse p55R but not the p75R are used to determine whether a candidate antibody blocks TNFα signalling through the p55R e.g. by inhibiting binding to the p55R. These cells are killed by human TNFα if sensitised with a protein synthesis inhibitor such as actinomycin D hence, for example, if a candidate antibody blocks binding of TNFα to the p55R it protects the cells from TNFα mediated cytotoxicity. Blocking antibodies can therefore be detected by determining cell viability at the end of the assay. The assay is described in detail in the Examples provided herein and in WO92/11383.

Alternatively the binding of TNFα to one of its receptors and the resulting receptor signalling can be detected using a cell based reporter gene assay using reporter genes such as, for example, a luciferase, β-galactosidase, alkaline phosphatase, or green fluorescent protein linked to at least the extracellular region (or a TNFα binding portion thereof) of TNFα receptors p55 or p75 to detect downstream gene expression following TNFα binding. Details of examples of such assays are provided in the Examples. A reduction in reporter gene expression is indicative of a candidate antibody blocking TNFα signalling through the receptor, for example by inhibiting binding to the receptor.

A number of different anti-TNFα antibodies from any suitable source may need to be screened using the methods described herein above to find one which selectively inhibits TNFα signalling through the p55R relative to the p75R. The present invention therefore provides a method of obtaining an anti-TNFα antibody that selectively inhibits the binding of TNFα to the p55R comprising:

a) obtaining at least one anti-TNFα antibody b) screening the antibody obtained in step (a) to determine whether the antibody selectively inhibits TNFα signalling through the p55R, for example by selectively inhibiting the binding of TNFα to the p55R and where necessary, repeating steps (a) and (b) until at least one selective antibody is found.

Preferably the antibody identified in step (b) of the method selectively inhibits the binding of TNFα to the p55R by greater than 45% and inhibits the binding of TNFα to the p75R by no more than 30%.

In one preferred embodiment, the antibodies obtained in step (a) of the method are obtained from an immunised animal, preferably using the methods described in for example, Babcook, J. et al., 1996, Proc. Natl. Acad. Sci. USA 93(15):7843-7848; WO92/02551; WO2004/051268 and International Patent Application number WO2004/106377.

Anti-TNFα antibodies that selectively inhibit TNFα signalling through the p55R, for example through inhibiting the binding of TNFα to the p55R may be identified or further tested, for example to determine therapeutically effective amounts in one or more animal models. Examples of suitable animals include, but are not limited to, mice, rats, rabbits, monkeys, guinea pigs, dogs and cats. Preferably, the animal used represents a model of an autoimmune or inflammatory disease, such as MS, diabetes, SLE, rheumatoid arthritis, autoimmune haemolytic anemia, myasthenia gravis, Grave's disease, idiopathic thrombocytopenic purpura, autoimmune thyroiditis, Behcets disease, Wegener's granulomatosis, psoriasis, psoriatic arthritis, ankylosing spondylitis or inflammatory bowel disease, including Crohn's disease and Ulcerative colitis.

In one example, the selective inhibition of TNFα signalling through the p55R can be determined by monitoring an amelioration or improvement in disease symptoms, a delayed onset or slow progression of the disease, for example but without limitation, a reduction in clinical score. Techniques known to physicians familiar with autoimmune disease can be used to determine whether a candidate agent has altered one or more symptoms associated with the disease.

A number of different models of autoimmune disease are known in the art, for example there are a number of disease models for MS ('t Hart and Amor 2003, Current Opinion in Neurology 16:375-83). In particular, experimental autoimmune encephalomyelitis (EAE) in ABH mice is considered to be a relevant model for MS in humans (Baker et al., 1990. Journal of Neuroimmunology, 28:261-270). Both acute and relapsing-remitting models have been developed.

The present invention also provides a specific region of the TNFα polypeptide wherein binding of an antibody to that region selectively inhibits TNFα signalling through the p55R, for example by inhibiting the binding of TNFα to the p55R relative to the p75R. This specific region or epitope of the TNFα polypeptide can be identified by any suitable epitope mapping method known in the art in combination with the antibody provided by the present invention. Examples of such methods include screening peptides of varying lengths derived from TNFα for binding to the antibody of the present invention with the smallest fragment that can specifically bind to the antibody containing the sequence of the epitope recognised by the antibody. The TNFα peptides may be produced synthetically or by proteolytic digestion of the TNFα polypeptide. Peptides that bind the antibody can be identified by mass spectrometric analysis. In another example, NMR spectroscopy can be used to identify the epitope of the present invention. Once identified, the epitopic fragment which binds an antibody of the present invention can be used, if required, to obtain additional antibodies which bind the same epitope.

In one embodiment there is provided a specific region or epitope of human TNFα wherein binding of antibody '462' or '463' or antibodies comprising one or more CDRs given in SEQ ID NOs 9, 10, 11, 12, 13, 14 and 21 to that region selectively inhibits TNFα signalling through the p55R.

Antibodies which cross-block the binding of the antibodies of the present invention to TNFα may be similarly useful in selectively inhibiting TNFα signalling through the p55R. In one embodiment therefore there is provided an antibody having specificity for human TNFα, which cross-blocks the binding of antibody '462' or antibody '463' or any antibody comprising one or more of the CDRs provided in SEQ ID NOs 9, 10, 11, 12, 13, 14 and 21 to human TNFα and/or is cross-blocked from binding to human TNFα by any one of those antibodies. In one embodiment an antibody according to this aspect of the invention binds to the same epitope as antibody '462' or antibody '463' or any antibody comprising one or more of the CDRs provided in SEQ ID NOs 9, 10, 11, 12, 13, 14 and 21. In one embodiment the antibody according to this aspect of the invention binds to an epitope which borders and/or overlaps with the epitope bound by antibody '462' or antibody '463' or any antibody comprising one or more of the CDRs provided in SEQ ID NOs 9, 10, 11, 12, 13, 14 and 21. Alternatively the antibody according to this aspect of the invention does not bind to the same epitope as antibody '462' or antibody '463' or any antibody comprising one or more of the CDRs provided in SEQ ID NOs 9, 10, 11, 12, 13, 14 and 21 or an epitope that borders and/or overlaps with said epitope.

Cross-blocking antibodies according to this aspect of the present invention can be identified using any suitable method in the art, for example by using competition ELISA or BIAcore where binding of the cross blocking antibody to human TNFα prevents the binding of antibody '462' or antibody '463' or any antibody comprising one or more of the CDRs provided in SEQ ID NOs 9, 10, 11, 12, 13, 14 and 21 or vice versa.

In one embodiment of this aspect of the invention there is provided an anti-TNFα antibody which selectively inhibits TNFα signalling through the p55R, which cross-blocks the binding of antibody '462' or antibody '463' or an antibody comprising one or more of the CDRs provided in SEQ ID NOs 9, 10, 11, 12, 13, 14 and 21 to human TNFα. In one embodiment the cross-blocking antibodies provided by this aspect of the invention inhibit the binding of antibody '462' or antibody '463' or an antibody comprising one or more of the CDRs provided in SEQ ID NOs 9, 10, 11, 12, 13, 14 and 21 to human TNFα by 80% or greater, preferably by 85% or greater, more preferably by 90% or greater, even more preferably by 95% or greater.

Alternatively or in addition, antibodies according to this aspect of the invention may be cross-blocked from binding to human TNFα by any one of antibody '462' or antibody '463' or an antibody comprising one or more of the CDRs provided in SEQ ID NOs 9, 10, 11, 12, 13, 14 and 21. Also provided therefore is an anti-TNFα antibody which selectively inhibits TNFα signalling through the p55R which is cross-blocked from binding human TNFα by antibody '462' or antibody '463' or an antibody comprising one or more of the CDRs provided in SEQ ID NOs 9, 10, 11, 12, 13, 14 and 21. In one embodiment the cross-blocking antibodies provided by this aspect of the invention are inhibited from binding human TNFα by antibody '462' or antibody '463' or an antibody comprising one or more of the CDRs provided in SEQ ID NOs 9, 10, 11, 12, 13, 14 and 21 by 80% or greater, preferably by 85% or greater, more preferably by 90% or greater, even more preferably by 95% or greater.

If desired an antibody for use in the present invention may be conjugated to an effector molecule. The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. In one example, anti-TNFα antibodies can be conjugated to an effector molecule, such as a cytotoxic agent, a radionuclide or drug moiety to modify a given biological response. For example, the therapeutic agent may be a drug moiety which may be a protein or polypeptide possessing a desired biological activity. Such moieties may include, for example and without limitation, a toxin such as abrin, ricin A, pseudomonas exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

In another example the effector molecules may be cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). In one example, the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures may be used to create such fusions, for example as described in WO 86/01533 and EP 0392745.

In another example the effector molecule may increase half-life in vivo, and/or enhance the delivery of an antibody across an epithelial barrier to the immune system. Examples of suitable effector molecules of this type include polymers, albumin, albumin binding proteins or albumin binding compounds such as those described in PCT/GB2005/002084.

In one example antibodies of the present invention may be attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods. See for example U.S. Pat. No. 5,219,996. Multiple sites can be used to attach two or more PEG molecules. Preferably PEG molecules are covalently linked through a thiol group of at least one cysteine residue located in the antibody fragment. Where a thiol group is used as the point of attachment appropriately activated effector molecules, for example thiol selective derivatives such as maleimides and cysteine derivatives may be used.

In another example the antibody is a modified Fab' fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. Preferably PEG is attached to a cysteine in the hinge region. In one example, a PEG modified Fab' fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab' fragment may therefore be approximately 40,000 Da.

Particular PEGylated antibody fragments also include those described in International patent applications WO2005003169, WO2005003170 and WO2005003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in SEQ ID NO:1; SEQ ID NO:3; SEQ ID NO:5; SEQ ID NO:7; SEQ ID NO:15, SEQ ID NO:17 and SEQ ID NO:19.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The present invention also provides a method for the treatment and/or prophylaxis of an autoimmune or inflammatory disease comprising administering a therapeutically effective amount of an anti-TNFα antibody that selectively inhibits TNFα signalling through the p55R, for example by selectively inhibiting the binding of TNFα to the p55R. The invention also provides the use of an anti-TNFα antibody that selectively inhibits TNFα signalling through the p55R, for example by selectively inhibiting the binding of TNFα to the p55R for the manufacture of a medicament for the treatment and/or prophylaxis of autoimmune or inflammatory disease.

The term 'treatment' includes either therapeutic or prophylactic therapy. When a reference is made herein to a method of treating or preventing a disease or condition using a particular inhibitor or combination of inhibitors, it is to be understood that such a reference is intended to include the use of that inhibitor or combination of inhibitors for the manufacture of a medicament for the treatment and/or prophylaxis of an autoimmune or inflammatory disease.

Antibodies which selectively inhibit TNFα signalling through the p55R, for example by inhibiting the binding of TNFα to the p55R can be used in the manufacture of a medicament for the treatment of any disease resulting from p55R mediated signalling, in particular autoimmune and inflammatory diseases. Particular autoimmune and inflammatory diseases include demyelinating autoimmune diseases of the CNS, multiple sclerosis (MS), diabetes, systemic lupus erythematosus (SLE), rheumatoid arthritis, autoimmune haemolytic anemia, myasthenia gravis, Grave's disease, idiopathic thrombocytopenic purpura, autoimmune thyroiditis, Behcets disease, Wegener's granulomatosis, psoriasis, psoriatic arthritis, ankylosing spondylitis, inflammatory bowel disease, including Crohn's disease and Ulcerative colitis.

As discussed herein, anti-TNFα antibodies which selectively inhibit TNFα signalling through the p55R for example by inhibiting the binding of TNFα to the p55R can be used in the treatment and/or prophylaxis of autoimmune and inflammatory diseases. For such use the agents will generally be administered in the form of a pharmaceutical composition.

Also provided is a pharmaceutical composition comprising an anti-TNFα antibody which selectively inhibits TNFα signalling through the p55R and a pharmaceutically acceptable carrier.

The composition will usually be supplied as part of a sterile, pharmaceutical composition that will normally include a pharmaceutically acceptable carrier. This composition may be in any suitable form (depending upon the desired method of administering it to a patient).

The antibodies of the invention are preferably administered to a subject by a variety of other routes such as orally, transdermally, subcutaneously, intranasally, intravenously, intramuscularly, intrathecally and intracerebroventricularly. The most suitable route for administration in any given case will depend on the particular antibody, the subject, and the nature and severity of the disease and the physical condition of the subject.

The antibodies of use in the invention may be administered in combination, e.g. simultaneously, sequentially or separately, with one or more other therapeutically active compounds, which may be for example other anti-autoimmune disease therapies or e.g. anti-cancer therapies.

Pharmaceutical compositions may be conveniently presented in unit dose forms containing a predetermined amount of an active agent of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

The dosage to be administered of an anti-TNFα antibody which selectively inhibits TNFα signalling through the p55R will vary according to the particular antibody, the type of autoimmune or inflammatory disease, the subject, and the nature and severity of the disease and the physical condition of the subject, and the selected route of administration; the appropriate dosage can be readily determined by a person skilled in the art. For the treatment and/or prophylaxis of autoimmune or inflammatory disease in humans and animals pharmaceutical compositions comprising antibodies can be administered to patients (e.g., human subjects) at therapeutically or prophylactically effective dosages (e.g. dosages which result in inhibition of an autoimmune or inflammatory disease and/or relief of autoimmune or inflammatory disease symptoms) using any suitable route of administration, such as injection and other routes of administration known in the art for clinical products, such as antibody-based clinical products.

The compositions may contain from 0.1% by weight, preferably from 10-60%, or more, by weight, of the inhibitor of the invention, depending on the method of administration.

It will be recognized by one of skill in the art that the optimal quantity and spacing of individual dosages of an inhibitor of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

The present invention is further described by way of illustration only in the following examples, which refer to the accompanying Figures, in which:

FIG. 1: p55TNFR and p75TNFR binding inhibition assay showing the effect of different anti-TNFα antibodies on the binding of TNFα to the p55R and the p75R.

Figure 2:
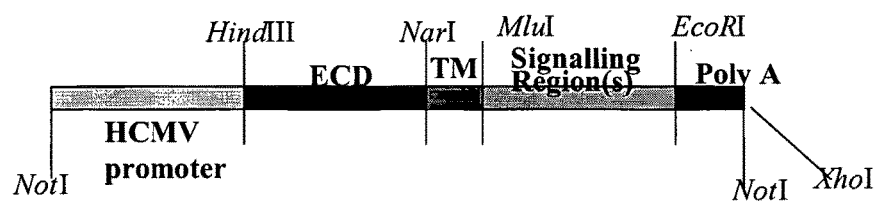

FIG. 2: shows the expression cassette cloned into the large NotI and XhoI restricted fragment of pBluescript® II SK(+) to generate the bioassay receptor shuttle vector.

Figure 3:
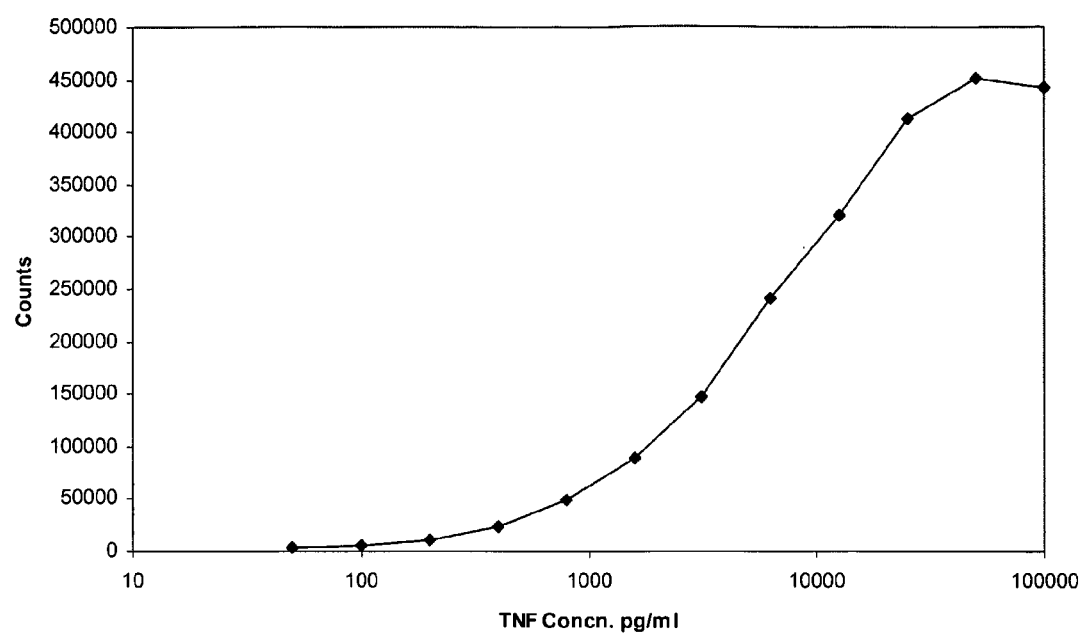

FIG. 3: shows a titration of the TNFα induced luciferase response from the p75/CD28-TCR zeta bioassay receptor.

Figure 4:
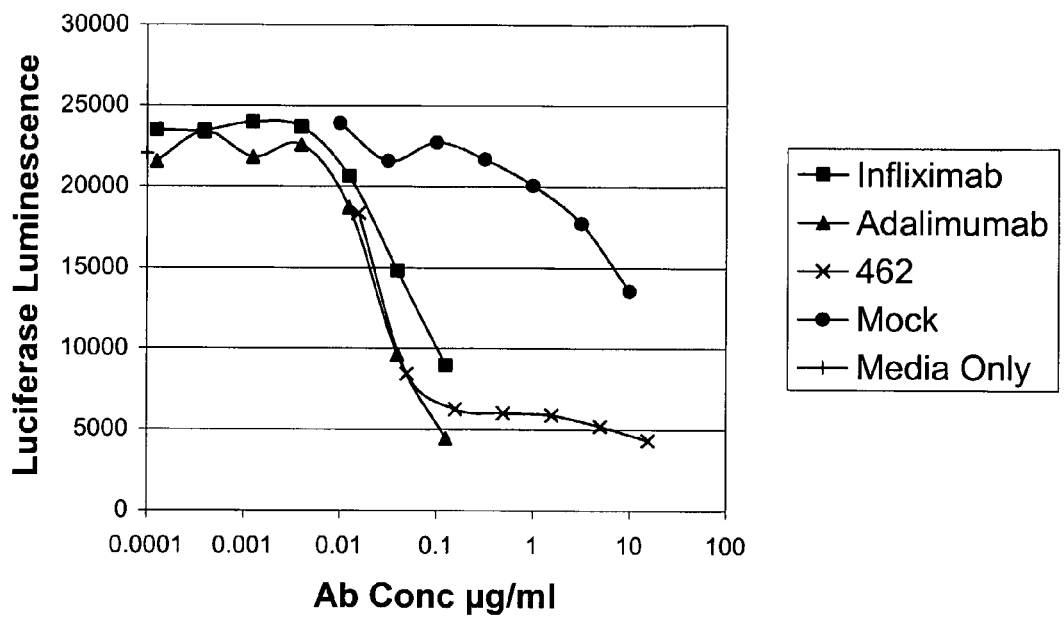

FIG. 4: shows the effect of antibody '462', infliximab and adalimumab on p55R signalling.

Figure 5:
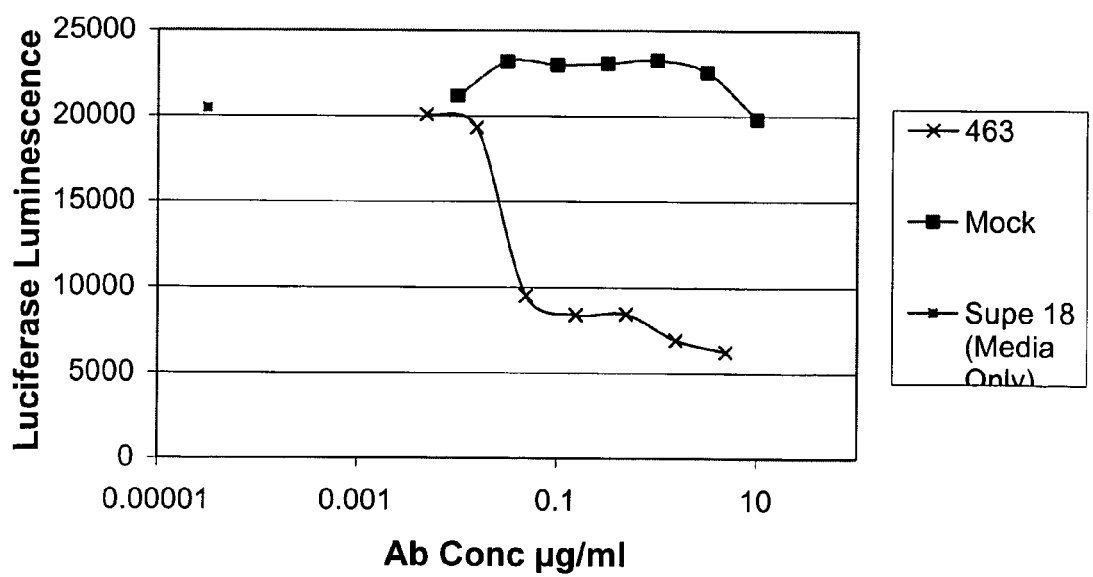

FIG. 5: shows the effect of antibody '463' on p55R signalling.

Figure 6:
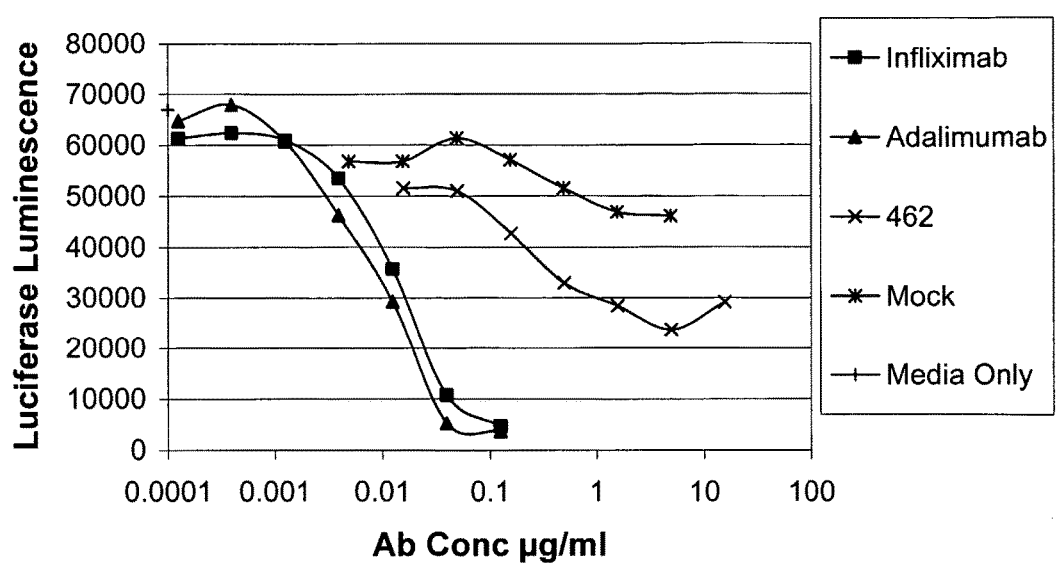

FIG. 6: shows the effect of antibody '462', infliximab and adalimumab on p75R signalling.

Figure 7:
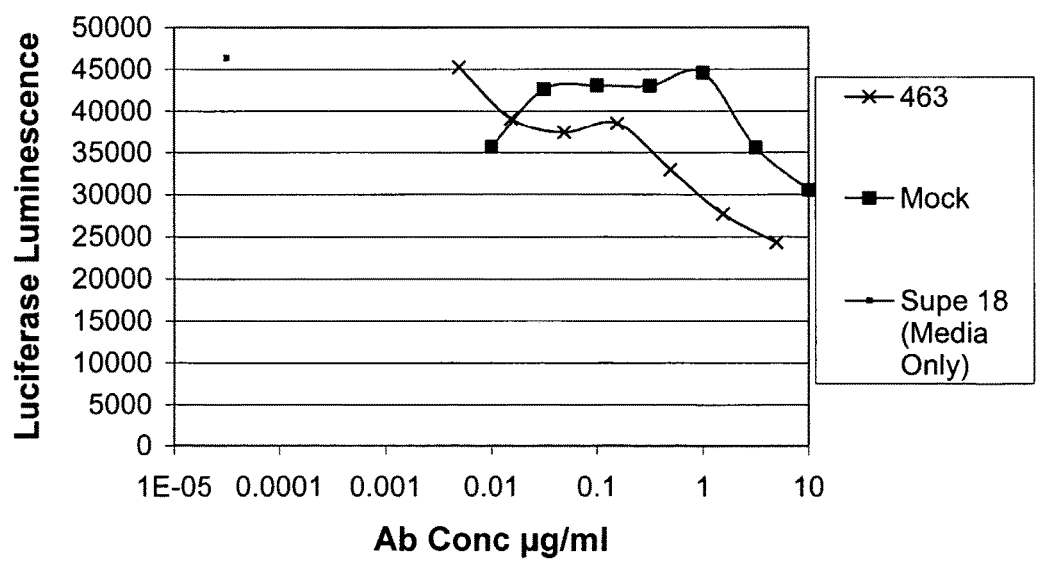

FIG. 7: shows the effect of antibody '463' on p75R signalling.

EXAMPLES

Example 1. Isolation of a Panel of Anti-TNFα Antibodies

Rats were immunised with soluble human recombinant TNFα. 4×5 ug at 3-4 week intervals initially in complete Freund's adjuvant by the sub-cutaneous route.

Spleen cells from one rat were then seeded into 40 microtitre plates at a cell density that ensures that any detected TNFα binding antibody is clonal. The cells were then cultured in T cell conditioned media (3%) and EL-4 cells ($5 \times 10^4$/well) for seven days. Seven days later supernatants from these plates were screened by ELISA for anti-TNFα antibodies using human TNFα (50 ng/ml) captured by a sheep polyclonal coated onto immunoplates. The supernatants from positive wells were then further tested in the L929 bioassay and the p55 and p75 receptor specific protein assays described below.

Example 2. TNFα Receptor Binding Inhibition Assays

L929 Assay

L929 cells (a mouse fibroblast cell line) that express the mouse p55TNFα receptor but not the p75TNFα receptor were used to assay for anti-TNFα antibodies that block binding of TNFα to this receptor. These cells are killed by human TNFα if sensitised with a protein synthesis inhibitor.

Cells were grown in standard tissue culture medium and seeded into 96 well tissue culture plates the day before being required in the assay. The culture medium was removed and test supernatants were added to individual wells. Human recombinant TNFα was then added to each well at 200-400 pg/ml in the presence of 1 µg/ml (final concentration) actinomycin D. The plates were then incubated overnight at 37° C.

On the following day the plates were washed gently in PBS and the cells fixed in methanol. They were then stained with 1% Crystal violet (live cells remain attached to the plates and take up the dye). Excess stain was washed off and the remaining stained cells solubilised in 30% acetic acid. The plates were then read at 570/405 nM.

Wells containing antibodies that block binding of TNFα to the mouse p55TNFR protect the cells from TNFα mediated cytotoxicity and show an enhanced signal compared with negative/control wells.

Positive wells were further tested in the p55R and p75R assays.

p55TNFR and p75TNFR Binding Inhibition Assay

Standard ELISA plates were coated with a sheep anti-human TNFα polyclonal antibody diluted 1/10,000. The plates were then blocked with PBS+1% BSA. Human TNFα was then added to each well at 25-50 ng/ml. After 1 hour unbound TNFα was washed off. Supernatants containing anti-TNFα antibodies were then added to replicate wells. In addition to one well of each replicate was added either human p55TNFR-Human Fc fusion protein or Human p75TNFR-Human Fc fusion protein. These were incubated for 1 hour and then washed to remove unbound receptor. Following this step an anti-Human IgG Fc peroxidase conjugated polyclonal antibody (Stratech Scientific) was added at 1/2000 dilution. The plates were left for 1 hr and then washed to remove unbound conjugate. TMB substrate was then added to each well, and the colour allowed to develop. Wells where the anti-TNFα antibodies have blocked binding of the receptor(s) can therefore be visualised.

FIG. 1 shows the percentage inhibition of TNFα binding to the p55TNFR and p75TNFR by four different anti-TNF antibodies. Antibody '3D6' inhibited binding of TNFα to the p55TNFR by 49.3% but only inhibited binding of TNFα to the p75TNFR by 14.6%. In contrast, antibody 22H3 for example inhibited binding of TNFα to the p55R and the p75R by 78.9 and 71.9% respectively. Antibody 3D6 therefore selectively blocks binding of TNFα to the p55R.

Example 3. Isolation of Further Selective Antibodies

Using the same rat population as Example 1 cultured B cells were screened to identify TNFα selective antibodies.

Human TNFα (Strathman Biotech GmbH) was biotinylated with a 10 fold molar excess of Sulfo-NHS-LC-LC-biotin (Pierce) for 1 hour at room temperature following the manufacturers' protocol. 5 μg of biotinylated TNFα was mixed with 50 μl of 9.95 micron superavidin coated microspheres (Bangs Beads) for 1 hour at room temperature in a volume of 500 μl (mix for 1×384-well plate). Beads were then washed 5 times in PEG block (1% PEG/0.1% tween/PBS) to remove unbound TNFα. TNFα-coated beads were then resuspended in approx. 4 ml PEG block and 10 μl added to each well of a 384-well plate. 10 μl of B cell culture containing rat antibody and 10 μl of goat-anti-rat IgG Fc gamma specific-Cy5 conjugate at 1:1666 dilution were added to the well containing beads. Plates were incubated at room temperature in the dark for 1 hour and then read on an Applied Biosystems 8200 machine. Applied Biosystems software was used to identify positive wells.

Approximately 1400 B cell culture plates were screened, which is approximately 140000 wells which represents approximately 2×10$^8$ B cells.

Of those screened 2500 wells contained antibodies which bound TNFα.

These were further screened for the ability to selectively block TNFα signalling through the p55R relative to the p75R using the assays described in Example 4. Antibodies were first screened for blocking p55R signalling and those that blocked signalling were then tested for the ability to block TNFα signalling through the p75R. Those antibodies which selectively blocked signalling through the p55R were isolated using the homogeneous fluorescence assay described in WO2004/051268 and heavy and light chain variable region genes were cloned via reverse transcription PCR from single rat B cells. Variable regions were expressed in recombinant IgG format to confirm binding and activity in signalling assays by sub-cloning into expression vectors containing the human antibody constant region genes (human kappa light chain and gamma-4 heavy chain in which the serine at position 241 has been changed to proline as described in Angal et al., Molecular Immunology, 1993, 30(1), 105-108) and a rat/human chimeric antibody expressed transiently in CHO cells. Transfections of CHO cells were performed using the lipofectamine procedure according to manufacturer's instructions (InVitrogen, catalogue No. 18324).

Two antibody sequences were obtained and these were termed, '462' and '463'. The V-region sequences of '462' are given in SEQ ID NOS:1, 2, 3 and 4. The variable region sequences without the leader sequences are provided in SEQ ID NOS: 5, 6, 7 and 8. The V-region sequences of '463' are given in SEQ ID NOS: 15, 16, 17 and 18. The variable region sequences without the leader sequences are provided in SEQ ID NOS: 19, 20, 7 and 8.

Example 4. TNFR Signalling Assays 4.1 p55R Signalling Assay p55 NFkB Luciferase Assay A549-ES-Luc cells were used for this reporter gene assay. A549 cells are an epithelial lung cell carcinoma that express the p55 TNF receptor and have been stably transfected with a vector comprising the E-selectin promoter (contains 3×NFkB binding sites) linked to the luciferase gene and a selectable marker for stable cell line generation.

A549-ES-Luc were grown in the following media:
RPMI 1640 (Phenol Free)
+10% FCS
+2 Mm Glutamine
+1 mg/ml G418 (Life Tech, 50 mg/ml stock)

A549-ES-luc cells were plated out into white opaque 96-well plates (Perkin Elmer) using a cell suspension of 1.5×10$^5$ cells/ml; 100 μl/well=15,000 cells/well. The cells were allowed to adhere overnight at 37° C./5% CO$_2$. The following day the media was aspirated and replaced with 100 μl of antibody in assay medium that has been pre-incubated for 30 minutes with human TNFα at 3 ng/ml final concentration. The cells were incubated for 5 hours at 37° C./5% CO$_2$. Luciferase expression was then assayed using a luciferase reporter gene assay kit (LucLite from Perkin Elmer). The plate was then read in a luminescence plate reader, the LJL Analyst.

4.2 p75 Signalling Assay

Jurkat cells that have been stably transfected with a vector containing a cassette coding for the p75R extra-cellular domain linked to the intra-cellular signalling regions of CD28 and TCR zeta was used to assay for p75 signalling. Within the same vector there are 5 binding sites for NFκB with a minimal E-selectin promoter region, this drives expression of the reporter gene luciferase, and a selectable marker for stable cell line generation. Stimulation of the p75 bioassay receptor with its ligand, human TNFα, leads via the CD28/zeta regions of the bioassay receptor, to the initiation of a signalling cascade within the cell. The signalling cascade induces NFκB activation and allows transcription of the luciferase reporter gene. Activation levels can then be measured in a luciferase assay. Antibodies that can block this activation will prevent expression of luciferase.

Construction of Receptor Expression Cloning Cassette and Shuttle Vector.

Intermediate shuttle vector containing the entire expression cassette necessary for the expression of the Bioassay receptor was used. This vector includes the cloning cassette devised in pBluescript SK+ (Stratagene) described previously (Finney et al., J. Immunol. 2004 172: 104). 5' to this cloning cassette is the HCMV promoter, and the SV40 polyadenylation signal is 3' to this cloning cassette. The cloning cassette consists of an extracellular domain (ECD) binding component, a transmembrane component and a signalling region component, and facilitates easy exchange of each individual component. Combining the following DNA fragments generated the shuttle vector:

A) The vector backbone of pBluescript II SK(−) (Stratagene) on a NotI to XhoI fragment
B) The cloning cassette described previously on a HindIII to EcoRI fragment
C) The HCMV promoter on a NotI to HindIII fragment
D) The SV40 polyadenylation signal on an EcoRI to XhoI fragment.

The generation of this shuttle vector is shown in FIG. 2.

Construction of Binding, Transmembrane and Signalling Component Fragments

Human p75 TNFα receptor extracellular domain binding component HindIII to NarI fragment.

A fragment comprising the leader sequence and extracellular domain residues 1 to 257 (GenBank ref:NM 001066) of the human p75 TNF-α receptor was PCR cloned using oligos 4023 (SEQ ID NO:22) and 4024 (SEQ ID NO:23) from plasmid pORF9-hTNFRSF1B (Invivogen). Oligo 4023 introduces a 5' HindIII site and Kosak sequence. Oligo 4024 introduces a 3' NarI site. The PCR product was then digested with restriction enzymes HindIII and NarI.

Human CD28 transmembrane and signalling region and human TCR zeta signalling region component NarI to EcoRI fragment.

A fragment comprising residues 135 to 202 of human CD28 transmembrane and signalling region and residues 31 to 142 of human TCR zeta intracellular region was digested from a plasmid previously described (Finney et al., J. Immunol. 2004 172: 104) with restriction enzymes NarI and EcoRI.

Construction of Bioassay Receptor Reporter Gene Vectors

The full length expression cassette for the Bioassay receptor was generated by combining the binding, transmembrane and signalling components described above in the shuttle vector described above. This was then subcloned into the reporter gene vector pNifty2-Luc(Invivogen). This vector contains a Luciferase reporter gene under control of a NF-kB inducible promoter and the selectable marker Zeocin™ for selection in both E. coli and mammalian cells. The Bioassay receptor expression cassette was removed from the shuttle vector on a NotI to NotI fragment and cloned into the NotI site of pNifty2-Luc.

Generation of Stable Bioassay Receptor Reporter Gene Cell Lines

Plasmid DNA of the vector was transfected into the human T cell leukaemia cell line, Jurkat E6.1 using the Amaxa Nucleofector device according to the manufacturers instructions (Amaxa Biosystems). Stable cell lines were then generated by culture in Zeocin™ at a concentration of 200 µg/ml.

Analysis of Anti-Human TNFα Antibody using a p75/CD28-TCR Zeta Bioassay Receptor.

A stable cell line expressing a bioassay receptor that comprises the human p75 TNFα receptor extracellular domain binding component, human CD28 transmembrane and signalling region, and human TCR zeta signalling region components was generated as described above. To these cells, a titration of human TNFα was added and the amount of Luciferase produced determined 4 hours later with a Luclite assay kit (Promega) according to the supplier's instructions. The TNFα induced Luciferase response from the p75/CD28-TCR zeta Bioassay receptor is shown in FIG. 3. A concentration of TNFα was selected from this titration and used to assess the ability of an anti-TNFα antibody to block Luciferase production via the p75/CD28-TCR zeta Bioassay receptor.

Assay Media:
500 ml DMEM (phenol free)
+10% Foetal Calf Serum
+2 mM Glutamine
+1 ml Normacin
+200 µg/ml zeocin
+1% enhancer solution, protease inhibitor Jurkat cells were plated out into white opaque 96-well plates using a cell suspension of $2 \times 10^6$ cells/ml. Antibodies were then added to the plate in the desired titration scale. The plate was incubated for 30 minutes at 37° C. and 10 µl of human TNFα ligand added to each well at a concentration of 30 ng/ml to give a final concentration of 3 ng/ml human TNFα in each well. The plate was incubated for 4 hours at 37° C. Luciferase expression was then assayed using a luciferase reporter gene assay kit (Luclite 1000 kit, Perkin-Elmer).

Results

The effect of antibody '462' and the commercially available anti-TNFα antibodies Adalimumab and Infliximab on Luciferase production in the p55R signalling assay is shown in FIG. 4. It is clear that all three antibodies inhibit TNFα signalling through the p55R. FIG. 5 shows that antibody '463' also inhibits TNFα signalling through the p55R.

The effect of antibody '462' and the commercially available anti-TNFα antibodies Adalimumab and Infliximab on Luciferase production in the p75R signalling assay is shown in FIG. 6. It is clear that only Adalimumab and Infliximab inhibit TNFα signalling through the p75R while antibody '462' leaves TNFα signalling through the p75R largely unaffected. FIG. 7 shows that antibody '463' also leaves TNFα signalling through the p75R largely unaffected. Both antibodies '462' and '463' were significantly less potent in the p75R signalling assay than in the p55R signalling assay.

Antibodies '462' and '463' therefore selectively inhibit TNFα signalling through the p55R.

---

The invention claimed is:

1. An anti-TNFα antibody or a fragment thereof that selectively binds TNFα, each comprising a heavy chain variable domain and a light chain variable domain, wherein the heavy chain variable domain comprises the sequence given in SEQ ID NO:9 for CDR-H1, the sequence given in SEQ ID NO:10 or SEQ ID NO:21 for CDR-H2 and the sequence given in SEQ ID NO:11 for CDR-H3 and wherein the light chain variable domain comprises the sequence given in SEQ ID NO:12 for CDR-L1, the sequence given in SEQ ID NO:13 for CDR-L2 and the sequence given in SEQ ID NO:14 for CDR-L3.

2. The anti-TNFα antibody or fragment thereof according to claim 1 comprising
(a) a heavy chain comprising SEQ ID NO:6 or SEQ ID NO:20 and
(b) a light chain comprising SEQ ID NO:8.

3. The antibody according to claim 1, wherein the antibody or fragment thereof is a CDR-grafted antibody.

4. The antibody according to claim 1.

5. The antibody according to claim 2.

6. The fragment according to claim 1 wherein the fragment is an Fab, Fab', F(ab')$_2$, or scFv fragment.

7. The antibody or fragment thereof according to claim 1 wherein the antibody or fragment thereof is conjugated to one or more effector molecule(s).

8. The antibody according to claim 7.

9. A pharmaceutical composition comprising an anti-TNFα antibody according to claim 1 and a pharmaceutically acceptable carrier.

10. A pharmaceutical composition comprising the fragment according to claim 1 and a pharmaceutically acceptable carrier.

* * * * *